(12) United States Patent
Kesti et al.

(10) Patent No.: US 11,633,518 B2
(45) Date of Patent: Apr. 25, 2023

(54) GRAFT SCAFFOLD FOR CARTILAGE REPAIR AND PROCESS FOR MAKING SAME

(71) Applicant: ETH Zurich, Zurich (CH)

(72) Inventors: Matti Kesti, Zurich (CH); Marcy Zenobi-Wong, Zurich (CH); Michael Muller, Zurich (CH)

(73) Assignee: ETH ZURICH, Zurich (CH)

( * ) Notice: Subject to any disclaimer, the term of this patent is extended or adjusted under 35 U.S.C. 154(b) by 354 days.

(21) Appl. No.: 16/735,751

(22) Filed: Jan. 7, 2020

(65) Prior Publication Data

US 2020/0139007 A1     May 7, 2020

Related U.S. Application Data

(62) Division of application No. 15/535,053, filed as application No. PCT/EP2015/079502 on Dec. 11, 2015, now Pat. No. 10,532,126.

(30) Foreign Application Priority Data

Dec. 11, 2014 (EP) .................................... 14197449
Mar. 9, 2015 (EP) .................................... 15158224

(51) Int. Cl.
| | |
|---|---|
| *A61L 27/20* | (2006.01) |
| *A61L 27/26* | (2006.01) |
| *A61L 27/38* | (2006.01) |
| *A61L 27/48* | (2006.01) |
| *B33Y 10/00* | (2015.01) |
| *A61L 27/46* | (2006.01) |
| *B33Y 30/00* | (2015.01) |
| *A61L 27/36* | (2006.01) |
| *B33Y 70/10* | (2020.01) |
| *B33Y 80/00* | (2015.01) |
| *A61L 27/52* | (2006.01) |
| *A61L 27/54* | (2006.01) |
| *G05B 19/4099* | (2006.01) |
| *B33Y 50/02* | (2015.01) |

(52) U.S. Cl.
CPC ............. *A61L 27/20* (2013.01); *A61L 27/26* (2013.01); *A61L 27/3612* (2013.01); *A61L 27/3817* (2013.01); *A61L 27/3852* (2013.01); *A61L 27/3856* (2013.01); *A61L 27/46* (2013.01); *A61L 27/48* (2013.01); *A61L 27/52* (2013.01); *A61L 27/54* (2013.01); *B33Y 10/00* (2014.12); *B33Y 30/00* (2014.12); *B33Y 70/10* (2020.01); *B33Y 80/00* (2014.12); *G05B 19/4099* (2013.01); *A61L 2300/414* (2013.01); *A61L 2430/06* (2013.01); *B33Y 50/02* (2014.12); *G05B 2219/35134* (2013.01); *G05B 2219/49007* (2013.01)

(58) Field of Classification Search
CPC ...... A61L 27/20; A61L 27/26; A61L 27/3817; A61L 27/46; A61L 27/48; A61L 27/52
See application file for complete search history.

(56) References Cited

U.S. PATENT DOCUMENTS

| | | | |
|---|---|---|---|
| 6,126,690 A | 10/2000 | Ateshian et al. | |
| 7,531,503 B2 | 5/2009 | Atala et al. | |
| 2009/0117087 A1* | 5/2009 | Carroll ................. | C12N 5/0656 424/572 |
| 2012/0089238 A1 | 4/2012 | Kang et al. | |

FOREIGN PATENT DOCUMENTS

| | | |
|---|---|---|
| AU | 2013204780 | 10/2014 |
| WO | 2011/119059 | 9/2011 |
| WO | 20140032748 | 3/2014 |

OTHER PUBLICATIONS

Chung et al. Bio-ink properties and printability for extrusion printing living cells. Biomater. Sci., 2013, 1, 763-773 (Year: 2013).*
James et al. Differential Effects of Transforming Growth Factor-beta 1 and -beta3 on Chondrogenesis in Posterofrontal Cranial Suture-Derived Mesenchymal Cells in Vitro. Plast Reconstr Surg. Jan. 2009 ; 123(1): 31-43.
Ferris et al. Modified gellan gum hydrogels for tissue engineering applications. Soft Matter, 9 (14), 3705-3711.
Lee et al. Optimizing gelling parameters of gellan gum for fibrocartilage tissue engineering. Journal of Biomedical Materials Research B: Applied Biomaterials. Aug. 2011 vol. 98B, Issue 2. p. 238-245.

* cited by examiner

*Primary Examiner* — Taeyoon Kim
(74) *Attorney, Agent, or Firm* — JMB Davis Ben-David

(57) ABSTRACT

The present invention relates to a method of providing a graft scaffold for cartilage repair, particularly in a human patient. The method of the invention comprising the steps of providing particles and/or fibres; providing an aqueous solution of a gelling polysaccharide; providing mammalian cells; mixing said particles and/or fibres, said aqueous solution of a gelling polysaccharide and said mammalian cells to obtain a printing mix; and depositing said printing mix in a three-dimensional form. The invention further relates to graft scaffolds and grafts obtained by the method of the invention.

18 Claims, 10 Drawing Sheets

Fig. 8A
Fig. 8B
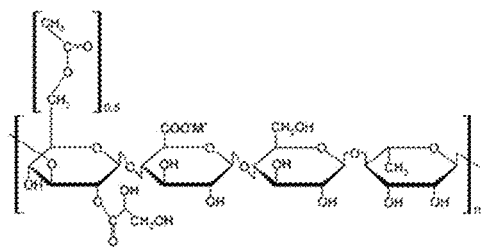
Fig. 9
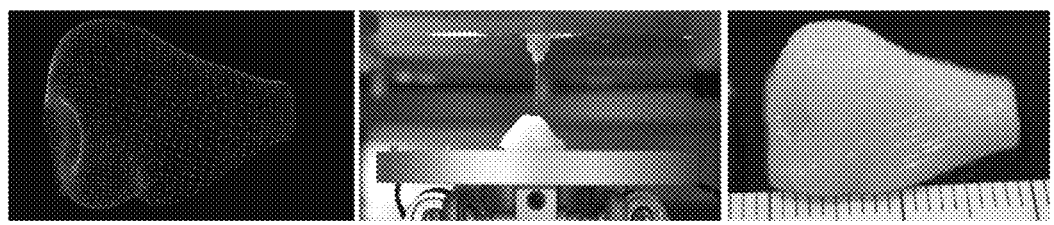

GRAFT SCAFFOLD FOR CARTILAGE REPAIR AND PROCESS FOR MAKING SAME

CROSS-REFERENCE TO RELATED APPLICATIONS

This is a divisional of U.S. patent application Ser. No. 15/535,053, filed Jun. 11, 2017, which is the US National Stage of International Patent Application No. PCT/EP2015/079502, filed Dec. 12, 2015, which in turn claimed the benefit of European Patent Application Nos. 14197449.3, filed Dec. 11, 2014, and 15158224.4, filed Mar. 9, 2015. The contents of the foregoing patent applications are incorporated by reference herein in their entirety.

FIELD

The present invention relates to a three dimensional graft, particularly for repair of craniofacial features and injured joints, and to a process of producing patient specific grafts using computer aided modelling and three-dimensional bio-printing with biocompatible inks.

BACKGROUND

Reconstruction of the nose and external ear in a patient specific manner are some of the greatest challenges in plastic surgery because of the complex, three-dimensional properties of the inner cartilage structure with regionally changing mechanical properties and overlaying skin. Auricular reconstruction is applicable to congenital deformities, microtia, melanoma related tissue sacrifice and injuries including accidents and severe burns. Ears are involved in approximately 90% of burns involving the head and neck. The mostly frequently used standard treatment for total auricular reconstruction in the United States and the European Union is based on a two- to three-stage surgical technique using autologous costal cartilage harvested from the sixth, seventh and eighth rib which is sculpted into an ear-like shape to the extent possible by the limited amount of harvested tissue. Sufficient amount of costal cartilage is generally achieved at age 10, delaying the reconstructive surgery. Another reconstruction method for ear reconstructive surgery is the use of silicone implants to avoid the need for costal cartilage harvesting. However placing an acellular scaffold under a thin layer of skin exposes the patient to a high risk of long-term complications. Additionally, it is impossible to provide for customized size and shape for each patient, and the reconstructed ear does not grow like the contralateral ear leading to asymmetry. Available reconstruction strategies involve several surgeries and their outcome is highly dependent of the expertise of the reconstructive surgeon. Donor side morbidity, collapse of the abdominal wall due to lack of costal cartilage support and severe pain related to the costal cartilage harvest are common complications.

Additionally, there is a large clinical need to repair osteochondral lesions, which occur as a result of sport injury, trauma and degenerative diseases such as osteoarthritis. Current methodologies to treat this involve transplantation of osteochondral grafts, which are either autologous or derived from bone banks. This treatment has several disadvantages including donor site morbidity, scarcity of donor tissue, surgical difficulty and the fact the graft consists of multiple pieces, each which can come loose or be mispositioned in the height.

In view of this state of the art, the objective of the present invention is to provide methods and means for providing patient specific grafts that improve on the above mentioned deficiencies of the state of the art. This objective is attained by the subject matter of the claims of the present specification.

SUMMARY

According to a first aspect of the invention, a method of providing a graft scaffold, particularly for use in a human patient, comprises the steps of:
  providing particles and/or fibres;
  providing an aqueous solution of a gelling polysaccharide;
  providing mammalian cells;
  mixing said particles and/or fibres, said aqueous solution of a gelling polysaccharide and said mammalian cells to obtain a printing mix;
  depositing said printing mix in a three-dimensional form.

According to another aspect of the invention, a method of providing a graft comprises the steps of:
  providing a graft scaffold by the method according to the first aspect of the invention, or any of its specific embodiments, and
  depositing said cell-free scaffold into a cell culture medium comprising mammalian cells, particularly cartilage cells, stem cells or cartilage precursor cells, in a cell culture step.

According to yet another aspect of the invention, a graft as obtained or obtainable by any of the preceding aspects of the invention, or any of their specific embodiments, is provided, particularly for use in a method for craniofacial or joint repair.

According to yet another aspect of the invention, a method of craniofacial or joint repair comprises the computer model of the patient specific graft modified for three-dimensional additive manufacturing with cartilage specific printing mix comprising at least one cytocompatible polymer, at least one of minced tissue or other additive particle and cells, the crosslinking being provided by spontaneous or externally triggered reaction of reactive groups and molecules embedded in the co-extruded material or in bio-ink internally, at least one of these types being present on at least one of the polymer, minced tissue and cells to reconstruct functional and native cartilage like tissue grafts.

According to an aspect of the invention, a method of creating internal polymer gradients, porosity and support regions for grafts better suited for mechanical loading of the tissue graft manufactured is provided by additive manufacturing methods.

According to an aspect of the invention, a method of creating sacrificial external support structures to aid in the printing of overhanging features of grafts is provided, wherein the sacrificial polymer is co-deposited with the printing mix and functions as a reservoir of crosslinking initiators to polymerize the printing mix and is removed after polymerization.

DETAILED DESCRIPTION OF THE INVENTION

A first aspect of the invention concerns a method of providing a graft scaffold, particularly in a human patient, comprising the steps of:
  providing an aqueous solution of a gelling polysaccharide;

providing at least one of:
  particles and/or fibres;
  mammalian cells;
  mixing said particles and/or fibres, said aqueous solution of a gelling polysaccharide and said mammalian cells to obtain a printing mix;
  depositing said printing mix in a three-dimensional form.

In certain embodiments, the printing mix comprises an aqueous solution of a gelling polysaccharide and particles. In certain embodiments, the printing mix comprises an aqueous solution of a gelling polysaccharide and fibres.

Fibres and/or particles, particularly when derived from cartilaginous tissue, may comprise factors aiding in supporting the growth of cells within the graft.

In certain embodiments, the printing mix comprises an aqueous solution of a gelling polysaccharide and both particles and fibres.

In certain embodiments, the printing mix comprises an aqueous solution of a gelling polysaccharide and cells. In certain embodiments, the printing mix comprises an aqueous solution of a gelling polysaccharide and cells and one or several growth factors. The inventors have surprisingly found that even in the absence of cartilaginous particles or fibres, the provision of gelling material and cells may be sufficient, particularly in presence of growth factors, to sustain cell viability and proliferation.

In certain embodiments, the printing mix comprises an aqueous solution of a gelling polysaccharide and particles and cells. In certain embodiments, the printing mix comprises an aqueous solution of a gelling polysaccharide and particles and fibres and cells.

In certain embodiments, said particles consist of, or comprise, tissue particles. In certain embodiments, said particles consist of, or comprise, cartilage particles. In certain embodiments, said particles consist of, or comprise, particles consisting of lyophilized cartilage tissue. In certain embodiments, said particles consist of, or comprise, human cartilage tissue. In certain preferred embodiments, said particles consist of, or comprise, autologous cartilage tissue. In certain preferred embodiments the particles can be clinical products of micronized matrix including BioCartilage, Amniofix, Alloderm-Cymetra, Cook Biotech Small Intestinal Muscosa (SIS) particles. In certain preferred embodiments the particles can be hydroxyapatite or calcium phosphate.

In certain embodiments, the particles and/or fibres are made of a synthetic polymer, particularly a polymer selected from the group consisting of polymers, or polymers derived from, polyethylene glycol, polypropylene glycol, gel forming poloxamers F108, F127, F68, F88, polyoxazolines, polyethylenimine, polyvinyl alcohol, polyvinyl acetate, polymethylvinylether-co-maleic anhydride, polylactide, poly-N-isopropylacrylamide, polyglycolic acid, polymethylmethacrylate, polyacrylamide, polyacrylic acid, and polyallylamine or co-polymers of these or block-copolymers of these.

In certain embodiments, the particles and/or fibres comprise or are predominantly or exclusively composed of minced tissue. In certain embodiments, the minced tissue is derived from tissue selected from the group consisting of auricular cartilage, nasal cartilage, nucleus pulposus, meniscus, trachea, nasal cartilage, rib cartilage, articular cartilage, synovial fluid, vitreous humor, brain, spinal cord, muscle, connective tissues, small intestinal submucosa and liver. In certain embodiments, the minced tissue is in the range of from 5 µm-50 µm, 50-200 µm and 200-1000 µm or a combination of these.

In certain embodiments, said gelling polysaccharide is gellan gum, acylated and/or sulfated gellan gum. In certain embodiments, said gelling polysaccharide is selected from guar gum, *cassia* gum, konjac gum, Arabic gum, ghatti gum, locust bean gum, xanthan gum, xanthan gum sulfate, carrageen, carrageen sulfate, or a mixture of any of the above gelling polysaccharides.

In certain embodiments, said solution of a gelling polysaccharide comprises a cytocompatible polymer as an additive in addition to the gelling polysaccharide, particularly a cytocompatible polymer selected from the group consisting of alginate, alginate sulfate, gellan sulfate, carrageen, carrageen sulfate, guar gum, *cassia* gum, konjac gum, Arabic gum, ghatti gum, locust bean gum, xanthan gum, xanthan gum sulfate, heparin, fibrin, heparin sulfate, elastin, tropoelastin, chondroitin sulfate, dermatan sulfate, hyaluronic acid, hyaluronan sulfate, cellulose, dextran, dextran sulfate, poly-l-lysine, chitosan, silk and collagen.

In certain embodiments, the additive is comprised in combination with gellan gum, acylated and/or sulfated gellan gum.

Gellan gum is a water-soluble polysaccharide produced by the bacterium *Pseudomonas elodea*. The repeating unit of the polymer is a tetrasaccharide, which consists of two residues of D glucose and one of each residues of L-rhamnose and D-glucuronic acid. The repeat has the following structure: $[D\text{-}Glc(\beta1\rightarrow 47D\text{-}GlcA(\beta1\rightarrow 4)Djhbn\text{-}Glc(\beta 877\rightarrow u8ir)L\text{-}Rha(\alpha 1\rightarrow 3)]_n$ "Acylated gellan gum" is a term known in the art and refers to gellan that comprises acetyl in some or all oxygen 5' positions and glycerylic acid in some of all oxygen 2' positions of the glucose unit. See FIG. 8: Acylated gellan (A) is a raw product gellan after bacterial fermentation and when it is purified acyl and glyseryl side chains can be cleaved (B). This enhances the gelation and different stiffness can be achieved. Certain embodiments of the present invention combine acylated and purified gellan together to achieve better flexibility for the structures.

In certain embodiments, the solution of a gelling polysaccharide comprises gellan gum or acetylated gellan gum, or a sulfation product of acylated gellan gum, as the gelling polysaccharide, and alginate, alginate sulfate, gellan sulfate, carrageen, and/or carrageen sulfate as a cytocompatible polymer additive.

In certain embodiments, an aqueous solution of a salt comprising monovalent, divalent and/or trivalent cations is added to said gelling polysaccharide to effect gelation.

In certain embodiments, said aqueous solution comprises between 10 and 150 mmol/l of divalent ions. In certain embodiments, said aqueous solution comprises strontium ions ($Sr^{2+}$). In certain embodiments, said aqueous solution comprises barium ions ($Ba^{2+}$). In certain embodiments, said aqueous solution comprises calcium ions ($Ca^{2+}$).

In certain embodiments, said aqueous solution comprises a total of between 10 and 150 mmol/l of divalent ions. In certain embodiments, said aqueous solution comprises between 10 and 150 mmol/l of strontium ions ($Sr^{2+}$), particularly between 15 and 50 mmol/l $Sr^{2+}$. In certain embodiments, said aqueous solution comprises between 10 and 150 mmol/l of barium ions ($Ba^{2+}$), particularly between 15 and 50 mmol/l $Ba^{2+}$. In certain embodiments, said aqueous solution comprises between 10 and 150 mmol/l of calcium ions ($Ca^{2+}$), particularly between 15 and 100 mmol/l $Ca^{2+}$.

In certain embodiments, said aqueous solution comprises a total of between 10 and 150 mmol/l of $Sr^{2+}$ and $Ba^{2+}$, particularly between 15 and 50 mmol/l of $Sr^{2+}$ and $Ba^{2+}$. In certain embodiments, said aqueous solution comprises a total of between 10 and 150 mmol/l of $Ca^{2+}$ and $Ba^{2+}$, particularly between 15 and 50 mmol/l of $Ca^{2+}$ and $Ba^{2+}$. In certain embodiments, said aqueous solution comprises a total of between 10 and 150 mmol/l of $Sr^{2+}$ and $Ca^{2+}$, particularly between 15 and 50 mmol/l of $Sr^{2+}$ and $Ca^{2+}$.

In certain embodiments, said solution of a gelling polysaccharide comprises a monosaccharide sugar or disaccharide sugar, particularly glucose, mannose or arabinose, at physiologic osmolarity. This addition can be important to safeguard viability of the cells embedded in the printing mix.

In certain embodiments, said particles and/or fibres consist of, or comprise,
- a biocompatible or cytocompatible polymer, and/or
- a bioresorbable polymer, particularly a polymer selected from the group consisting of PLA (polylactic acid or polylactide), DL-PLA (poly(DL-lactide)), L-PLA (poly(L-lactide)), polyethylene glycol (PEG), PGA (polyglycolide), PCL (poly-ε-caprolactone), PLCL (Polylactide-co-ε-caprolactone), dihydrolipoic acid (DHLA), alginate and chitosan, and/or
- a synthetic polymer, particularly a polymer selected from the group consisting of polymers, or polymers derived from, polyethylene glycol, polypropylene glycol, polaxomers, polyoxazolines, polyethylenimine, polyvinyl alcohol, polyvinyl acetate, polymethylvinylether-co-maleic anhydride, polylactide, poly-N-isopropylacrylamide, polyglycolic acid, polymethylmethacrylate, polyacrylamide, polyacrylic acid, and polyallylamine.
- natural fibers, particularly selected from elastin, resilin, and silk and their derivatives;
- A biocompatible conductive material, particularly transition metal tantalum and conductive polymer polypyrrole (PPy).

In certain embodiments, particles are formed from a biopolymer mentioned above in oil emulsion or by precipitation. In certain specific embodiments, such biopolymer is alginate.

In certain embodiments, said tissue particles are derived from tissue selected from the group consisting of auricular cartilage, nasal cartilage, nucleus pulposus, meniscus, trachea, nasal cartilage, rib cartilage, articular cartilage, synovial fluid, vitreous humor, brain, spinal cord, muscle, connective tissues, small intestinal submucosa and liver.

In certain embodiments, the cytocompatible polymer is a natural polymer.

In certain embodiments, the cytocompatible polymer is gellan gum of varying acylation degree, particularly acylation ranging between 100% to 10% acylation, with 100% being high, and optionally comprises an additive selected from the group consisting of alginate, alginate sulfate, heparin, fibrin, heparin sulfate, elastin, tropoelastin, chondroitin sulfate, dermatan sulfate, hyaluronic acid, hyaluronan sulfate, cellulose, dextran, dextran sulfate, poly-l-lysine, chitosan, silk and collagen of varying type and sulfated versions of these.

In certain embodiments, ≥90%, ≥95%, or ≥98% of said particles are in the range of from 5 µm-1000 µm, particularly from 5 µm to 50 µm, 5 µm to 200 µm, 50 µm-200 µm or 200 µm to 1000 µm.

In certain embodiments, said fibers are sized in the range of 5 µm-50 µm and 50-500 µm in length having an aspect ratio ranging between 2-1000, particularly an aspect range of 10-500, more particularly 100-500, 100-1000, 200-1000 or from 500 to 1000. In certain embodiments, silk fibres are used having a diameter of 1 µm or less, and a length of 500 to 1000 µm or more. The aspect ratio for the purpose of the term's use in the context of the present specification is defined as the ratio of fiber length to diameter.

In certain embodiments, said mammalian cells are cartilage cells, cartilage precursor cells or stem cells capable of differentiating into cartilage precursor cells or cartilage cells.

In certain embodiments, the mammalian cells are selected from the group consisting of primary autologous chondrocytes, primary allogenic chondrocytes, chondroprogenitor cells, chondroblasts, mesenchymal stem cells, induced pluripotent stem cells and adipose-derived stem cells.

In certain embodiments, the printing mix comprises:
- 1-6% (w/v), particularly approx. 3% (w/v) of said gelling polysaccharide;
- 0.5-10% (w/v), particularly approx. 4% (w/v) of said particles,
- optionally, 0.5-8% (w/v), particularly approx. 2% (w/v) of said additive.

In certain embodiments, the printing mix comprises:
- approx. 3% (w/v) of gellan gum;
- approx. 4% (w/v) of cartilage tissue particles,
- approx. 2% (w/v) of alginate, 10 ng/ml TGBF3
- $10^6$ to $10^7$ cartilage cells per ml.

In certain embodiments, the printing mix is deposited together with a sacrificial polymer. This allows the generation of overhanging structures, such as are especially important in shaping certain features of the nose and ear.

In certain embodiments, the printing mix is deposited onto a sacrificial polymer scaffold.

In certain embodiments, the sacrificial polymer scaffold is co-deposited with the printing mix.

In certain embodiments, the sacrificial polymer mix and/or scaffold comprises divalent cations or other agents of gelation/polymerization.

By diffusing out of the sacrificial polymer mix, into the printing mix, these cations or other agents of gelation/polymerization allow for a rapid formation of the three dimensional structure of the scaffold.

In certain embodiments, the three dimensional form and/or said sacrificial polymer scaffold is derived by 3-D-printing methods, particularly on the basis of a three dimensional computer model of a contralateral organ of said patient.

In certain embodiments, the three dimensional model is obtained by computed tomography, magnetic resonance imaging, laser scanning or utilizing three dimensional cameras.

In certain embodiments, the computer model is created to support load bearing in gradients and to create internal structures for better cell survival and porosity.

In certain embodiments, the polymer scaffold is derived by additive manufacturing methods.

In certain embodiments, the additive manufacturing method is ink jet printing, bioprinting, extrusion printing or layer-by-layer method.

In certain embodiments, the polymer scaffold is characterized by internal polymer gradients, porosity and support regions.

In certain embodiments additional polymers are added to increase the matrix liquid viscosity so that the ink can be extruded consistently and is not blocked due to filter pressing phenomena.

In certain embodiments, the sacrificial polymer is removed prior or subsequent to said cell culture step.

In certain embodiments, the tissue particles and/or bioink comprise a growth factor or a combination of growth factors, particularly selected from BMP-2, BMP-7, TGF-β1, TGF- β2, TGF-β3, and/or FGF-2, and/or mitogenic factors, particularly IGF-1, to promote healing and regeneration.

In certain embodiments, growth factors can be directly loaded into the bioink mixture. In certain embodiments, the concentration of said growth factor(s) is in the range of from 0.1-5 mg/ml, 5-50 ng/ml or 50-500 ng/ml of one growth factor or a combination of several growth factors. In certain embodiments, the growth factors are selected from BMP-2, BMP-7, TGF-β 1, 2, 3, IGF-1 and/or FGF-2.

In certain embodiments, the printing mix, particularly the particles, comprise additional components, particularly components selected from growth factors, antioxidants, cytokines, drugs and biologics.

In certain embodiments, the sacrificial polymer concludes an agent for initiating the crosslinking, said agent being a monovalent, divalent and trivalent cation, enzyme, hydrogen peroxide, horseradish peroxidase, radiation polymerizable monomers such as lithium phenyl-2,4,6-trimethylbenzoylphosphinate.

In certain embodiments, crosslinking initiating groups are present in the printing mix, particularly selected from groups that participate in light exposure, cation-mediated crosslinking and enzyme-mediated crosslinking.

Another aspect of the invention concerns a method of providing a graft repair, comprising the steps of:
  providing a graft scaffold by the method according to any one of the preceding claims, and
  depositing said cell-free scaffold into a cell culture medium comprising mammalian cells, particularly cartilage cells, stem cells or cartilage precursor cells, in a cell culture step.

Another aspect of the invention concerns a graft scaffold obtainable by, or obtained by, the method according to any one of the preceding methods of the invention, or any specific embodiment or combination of features provided by the specific embodiments.

The present invention provides patient-specific craniofacial reconstructive grafts produced by additive manufacturing methods. The cartilage tissue graft abolishes the need for cartilage harvesting thus decreasing patient discomfort, reducing the surgical time and allowing better replication of shape, size and mechanical flexibility. Furthermore faster tissue regeneration and increased cell proliferation can be achieved to enhance the surgical recovery. For craniofacial applications this technique can be combined with currently used skin augmentation treatment (i.e. expanders) or other natural or synthetic skin grafts.

Printing

According to the present invention, patient specific auricular and nasal grafts are produced based on the three-dimensional scanned models from the patient by utilizing additive manufacturing methods such as but not limited to extrusion printing, inkjet printing and other layer-by-layer deposition methods. Clinical computed tomography (CT), magnetic resonance imaging (MRI) or other three dimensional imaging tools such as laser scanners, 3D cameras or combinations of these are used to produce the computerized model of the patient specific implant. For ear reconstruction, the image can be mirrored to produce a computational model precisely mimicking the contralateral ear for tissue graft production. For ear and nose reconstruction a library of graft models can be used to provide choice of grafts for the patient especially in a case where a normal contralateral scan cannot be performed. These methods can lead to better cosmetic and aesthetic results when specific size reductions tools are used to reduce the dimensions of the cartilage framework by the thickness of the skin layer to achieve a final graft of correct size. Additive manufacturing methods can be utilized in creation of these constructs in high precision and in sterile conditions. Furthermore internal support structures and porosity for cell survival in large constructs can be added in a patient-specific shape and/or stiffness depending on the patient's needs. Avascularized cartilage can be designed to host vascular structures for over laying skin and other tissues in its proximity to prevent necrosis. The printed cartilage framework can be used as a bioactive template for the construction of overlying tissues, releasing growth factors and other secretory molecules to enhance the viability of neighboring cells. This release can be specially designed by having sulfated polymers in the mixture to bind growth factors to the proximity of the cells and slowly releasing the molecules.

In certain embodiments, the 3D form can be created as a computer model to support load bearing in gradients and to created internal structures for better cell survival and porosity.

The disclosure is further described with reference to the following figures and non-limiting examples, which depict particular embodiments.

Figure 3:
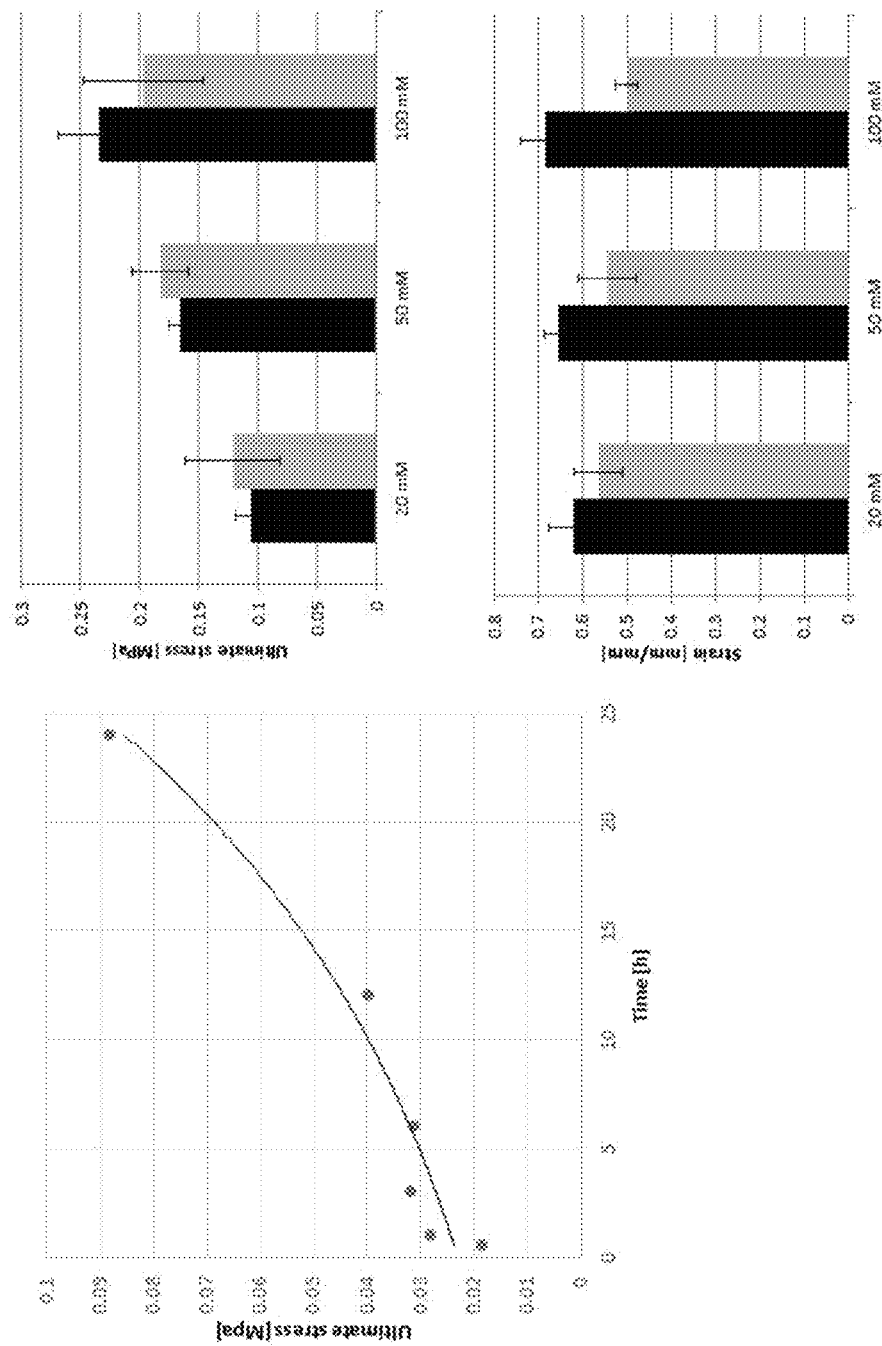

FIG. 3 illustrates the time dependency of the mechanical properties with the 20 mM strontium chloride solution where specimens (n=6) average ultimate stress at failure for each time point was measured in tension (left). Furthermore, the concentration of cations (black=calcium chloride and grey=strontium chloride) has similar effect on crosslinking despite the cationic source (right, top and bottom). It can be concluded that the mechanical properties are highly dependent on the cation concentration and crosslinking time.

Figure 4:
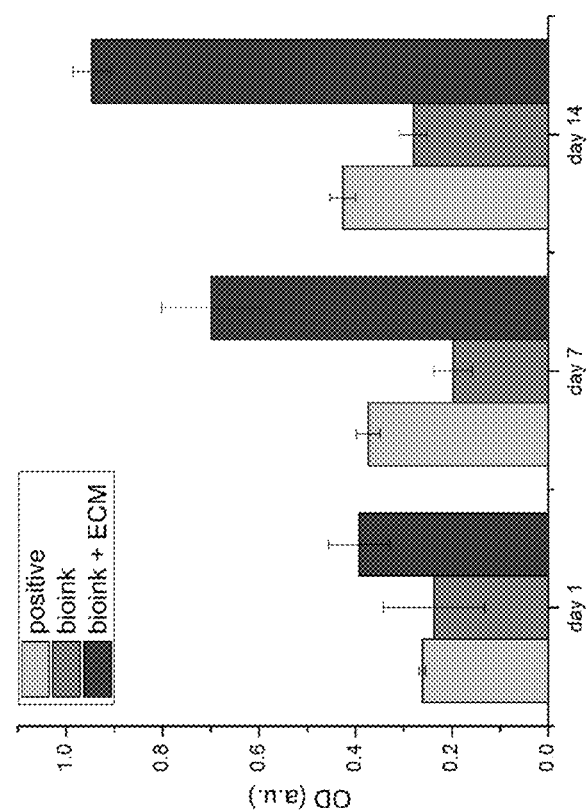

FIG. 4 is a graph illustrating the metabolic activity of the chondrocytes embedded into the printing mix material in printing process. Metabolic activity assay (Promega MTS one solution assay was performed in several time points analyzed with a plate reader (Synergy H1, Biotek). Positive control was alginate 1% (light gray), printing mix material corresponds to printing mix material without tissue particles (gray) and printing mix material+ECM (dark gray) consists of cartilage extra cellular matrix particles <100 μm in diameter. All conditions were analyzed in triplicates.

Figures 5A, 5B:
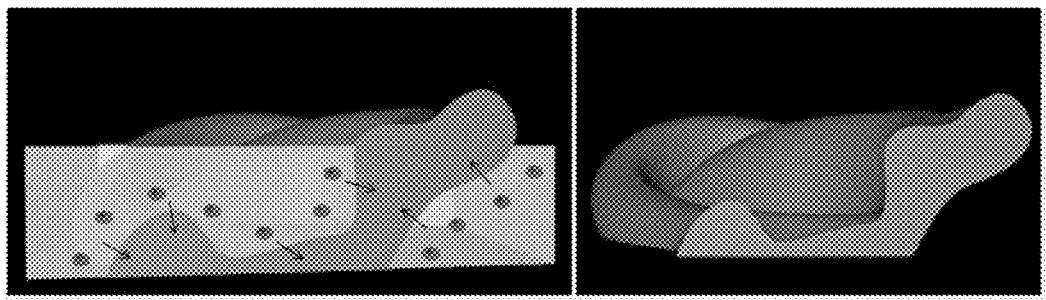

FIGS. 5A and 5B illustrate the co-deposited support structure providing initial crosslinking molecules such as cations from any source, enzyme, protein or other activating molecule that initiates the crosslinking cascade (FIG. 5A) and the final construct with overhanging features after elution of the support (FIG. 5B).

Figure 6:
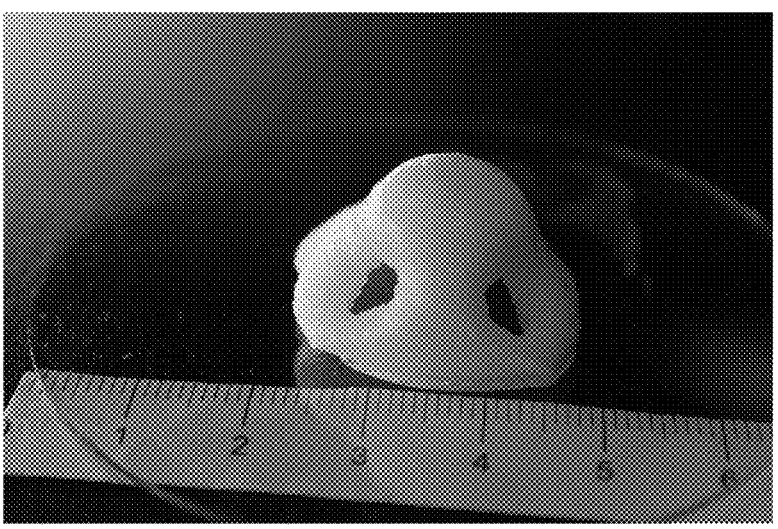

FIG. 6 is a photograph of an intact native size tissue engineered nose construct composed of particles, gellan gum, and alginate. Construct was fabricated utilizing three-dimensional bioprinting in less than 17 minutes. Space between the lines represents 1 mm.

Figure 7:
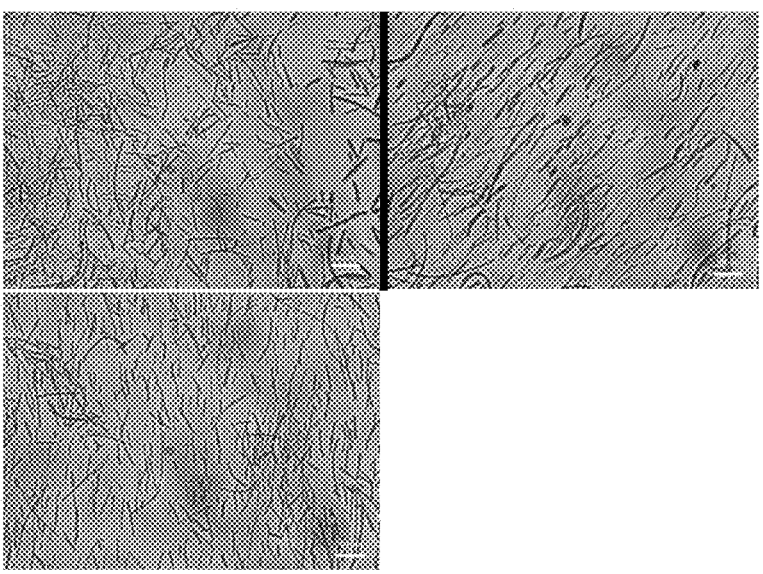

FIG. 7 is a bright field microscopy image showing 10% PMMA fiber orientation in 3% gellan gum before shear (left), after uniaxial shear in two directions corner to corner (middle) and after uniaxial shear vertically. Scale bar is 50 microns.

FIGS. 8A and 8B illustrate the gellan gum composition of high acylated gellan (FIG. 8A) and non acylated gellan (FIG. 8B).

FIG. 9 illustrates the conversion of patient specific three dimensional model during the printing process into tissue engineered nasal graft from left to right. Space between the lines represents 1 mm.

Figure 10A:
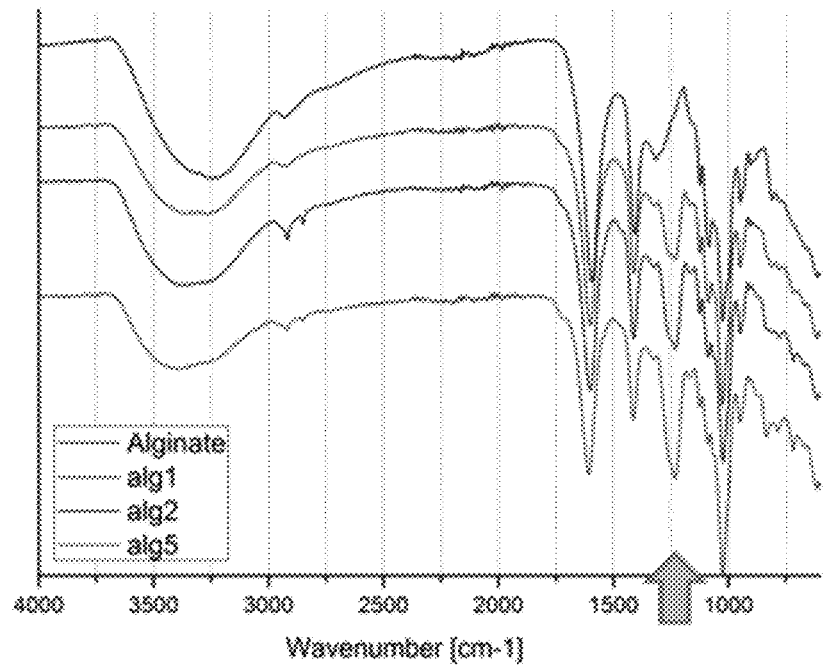
Figure 10B:
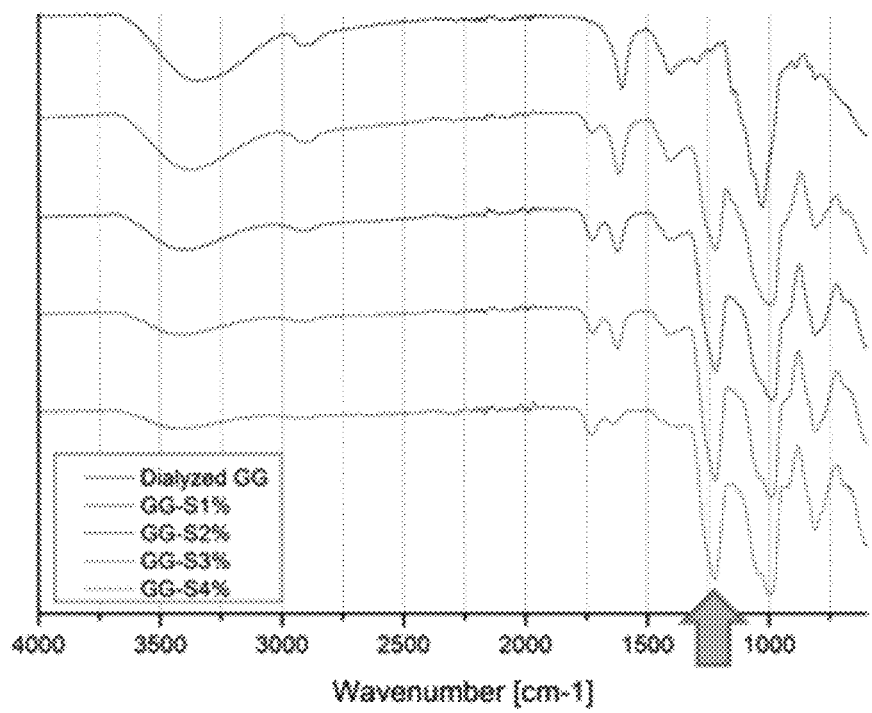

FIGS. 10A and 10B show the Fourier transform infrared spectroscopy (FTIR) results of several degrees of sulfation in polymer backbones of alginate (FIG. 10A) and gellan gum (FIG. 10B). Arrow in 1300 $cm^{-1}$ marks the peak of sulfation. In higher degrees of sulfation in polymer the growth factor binding is increased leading to better delivery of molecules.

Figure 11A:
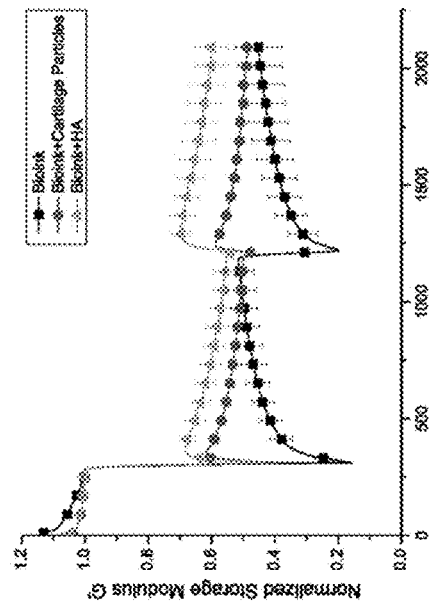
Figure 11B:
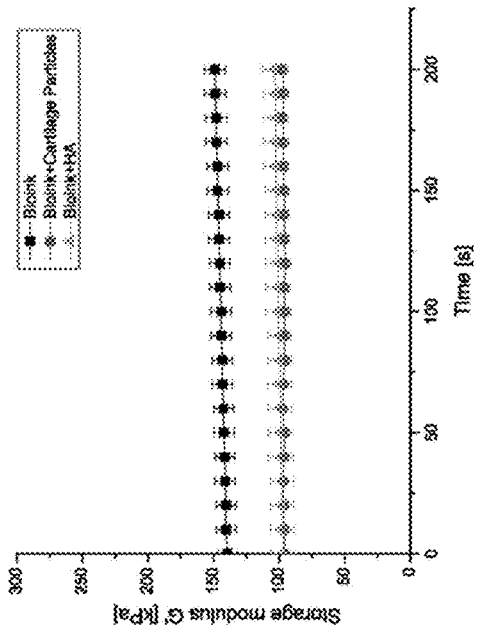
Figure 11C:
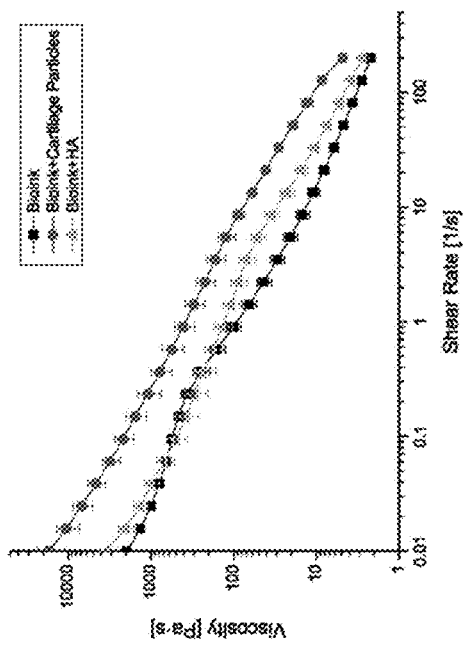
Figure 11D:
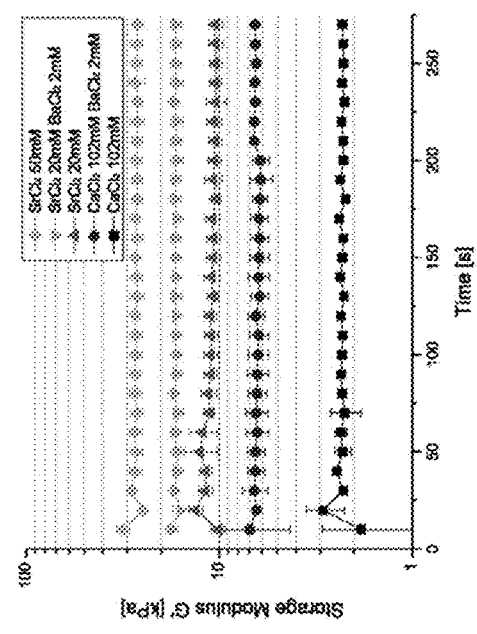

FIGS. 11A-11D show the result of a rheological characterization of the bioink compositions with and without particles. Shear thinning was measured in rotation (FIG. 11A), shear recovery in oscillation after shear of 1 second ($100^{-8}$ shear rate) for two cycles (FIG. 11B), Bioink alone was ionically crosslinked with several cation conditions (FIG. 11C), and maximum storage modulus G' of the samples crosslinked for 30 minutes with 20 mM $SrCl_2$ (FIG. 11D). Error bars represent standard deviation.

Figure 12A:
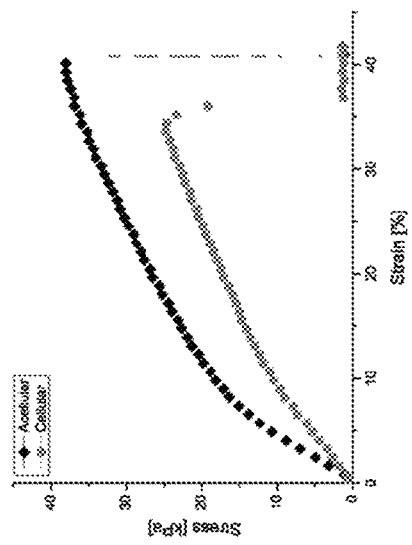
Figure 12B:
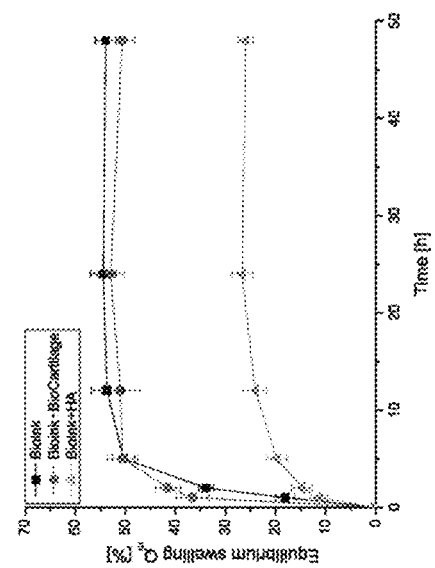

FIGS. 12A-12D show the result of a determination of the tensile and swelling properties of the printed constructs. Tensile testing was performed on printed dumbbell specimens where the nozzle path is shown by the black lines and the printed structure is shown after swelling (FIG. 12A). Representative stress-strain curves where failure occurred in the central region of the specimen (FIG. 12B). Swelling behavior of the bioink compositions based on equation (2) and (3) to evaluate total water retention (FIG. 12C) and water retention after crosslinking (FIG. 12D) respectively. The smallest divisions on the ruler are 1 mm and error bars represent standard deviation.

Figure 13C:
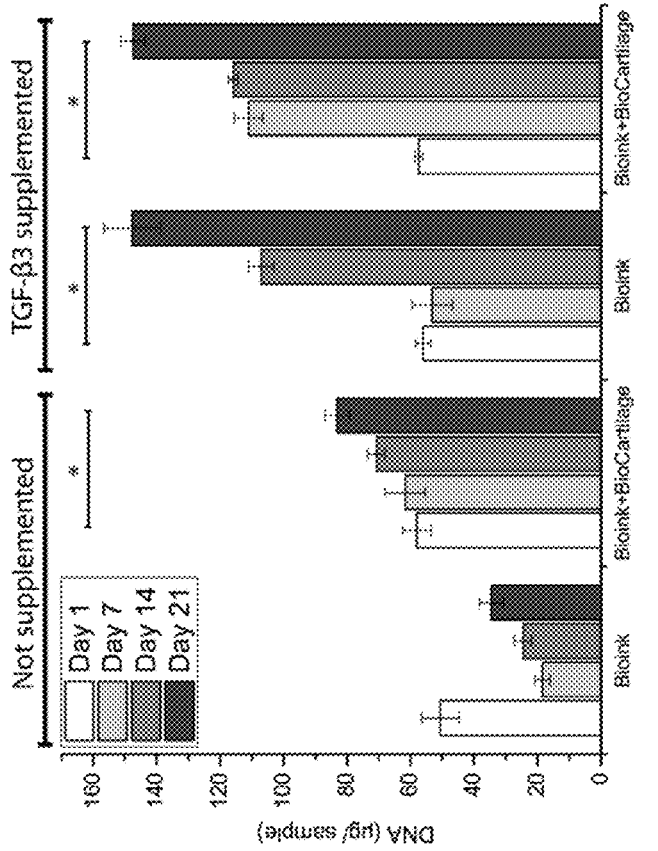
Figure 13A:
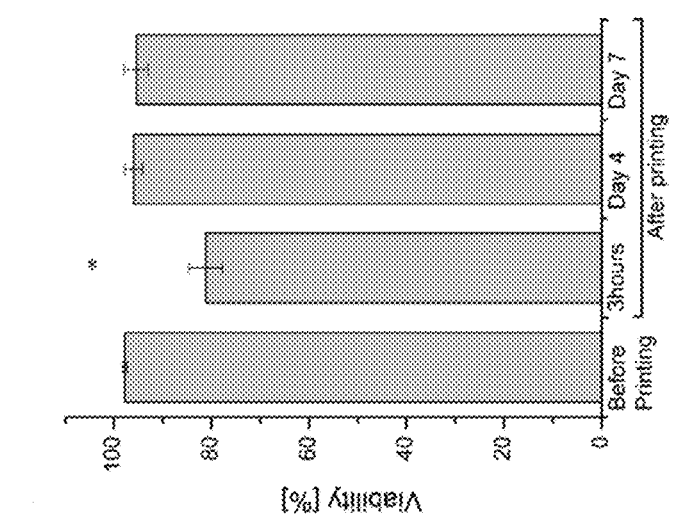
Figure 13B:
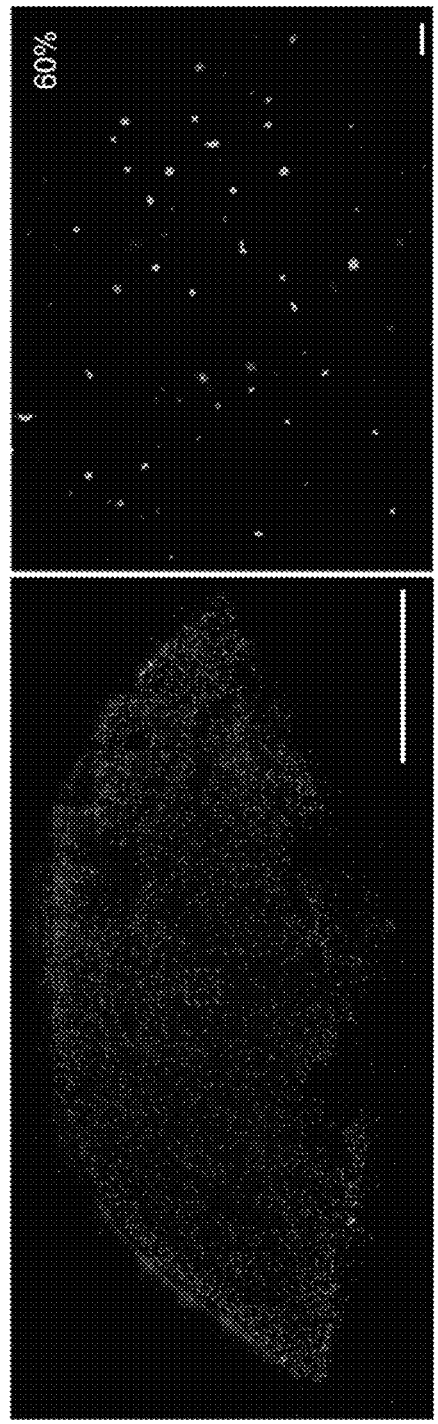

FIGS. 13A-13C show the result of a determination of cell viability of printed constructs and the cell proliferation assay. Viability after printing one layer thick discs was evaluated with live dead staining (FIGS. 13A and 13B) where 80% viability was observed $3h$ after printing, which recovered to 97% by day 4. To assess viability in a large structure, a young adult size nose was printed and the viability was evaluated from a central slice (diffusion distance ~5 mm) evaluated by live dead staining. A cell viability of 60% was observed. Scale bar 5 mm (FIG. 13B, left), and 50 μm (FIG. 13B, right). Additionally, cell number in casted disks were evaluated with DNA quantification (FIG. 13C) where a statistically significant increase in DNA from day 1 to day 21 was observed with Bioink+Cartilage particles and both TGF-β3 supplemented compositions. Error bars represent standard deviation and level of significance was ($p<0.05$).

DETAILED DESCRIPTION

Material

The bioink material comprises at least one cytocompatible polymer and at least one of particles and cells, the crosslinking being provided by spontaneous or externally triggered reaction of reactive groups and molecules, at least one of these types being present on at least one of the polymer, minced tissue and cells. The cytocompatible polymers (hereinafter referred to as "the polymers") for use in this method may be any suitable polymers with the necessary cytocompatibility, that is, their presence is not harmful to cells. They may be natural (biopolymers) or synthetic materials, or combinations of these. The necessary reactive groups allowing the crosslinking may be already present on the polymers, or the polymers may be modified to include such groups. Typical non-limiting examples of natural polymers include alginate, alginate sulfate, heparin, fibrin, heparin sulfate, elastin, tropoelastin, chondroitin sulfate, dermatan sulfate, hyaluronic acid, hyaluronan sulfate, cellulose, dextran, dextran sulfate, poly-l-lysine, chitosan, gelatin, gellan gum of varying acylation degree, gellan sulfate, guar gum, *cassia* gum, konjac gum, Arabic gum, ghatti gum, locust bean gum, xanthan gum, xanthan gum sulfate, carrageen, carrageen sulfate, silk and collagen of varying type. All sulfated versions of these polymers are included.

Typical non-limiting examples of synthetic polymers include, but are not limited to, polymers, or polymers derived from, polyethylene glycol, polypropylene glycol, polaxomers, poly oxazolines, polyethylenimine, polyvinyl alcohol, polyvinyl acetate, polymethylvinyl ether-co-maleic anhydride, polylactide, poly N-isopropylacrylamide, polyglycolic acid, poly methylmethacrylate, polyacrylamide, polyacrylic acid, and polyallylamine.

By "at least one" of the groups being present on at least one of the polymer, particles and cells, is meant that the added reactive groups may be present on all or any of these entities.

Particles incorporated to polymer solution can consist of but are not limited to extracellular matrix tissue particles, loaded or unloaded beads and fibers in size range between 5-500 microns.

Crosslinking

The formation of hydrogel based on the material combination, particles and cells can be initiated by many factors or agents, including but not limited to mono-, di-, trivalent cations, enzymes and radical initiators. Additionally, physical and physical-chemical methods may be employed, for example, treatment in low or high pH solution and different temperature regions during the manufacturing process.

In certain embodiments, either one of said printing mix and said polymer scaffold comprises reactive groups covalently attached thereto, particularly reactive groups facilitating linking of said printing mix, or its constituent components, to said particles, by crosslinking by spontaneous or externally triggered reaction, wherein reactive groups are present on at least one of the polymer, minced tissue and cells to reconstruct functional and native cartilage like tissue grafts.

Particles

The size of the minced tissue to be used may be any suitable size, but in a particular embodiment, it is from 5 microns-500 microns, so that it can be extruded without clogging the dispensing unit such as needle or valve. The minced tissue for use in the method may be any suitable tissue, but it is advantageously tissue of a similar or identical nature to that of the cartilage. Exemplary and non-limiting examples of suitable tissue include articular cartilage, nucleus pulposus, meniscus, trachea, nasal cartilage, rib cartilage, ear cartilage, synovial fluid, tracheal cartilage, vitreous humor, brain, liver, spinal cord, muscle, connective tissues and subcutaneous fat, intrapatellar fat pad, small intestinal submucosa. A particular example is tissue with high content of elastin and glycosaminoglycan, particular examples being any type of cartilage, nucleus pulposus and meniscus. The tissue may be minced by any suitable method, exemplary and non-limiting methods including homogenizing, cryomilling, dry milling, cutting, chopping, crushing and slicing. The tissue may be subject to decellularization to remove epitopes which can cause acute inflammatory responses and pathogens including HIV. Recently, decellularized tissues, that is, tissue in which the cells have been killed and their remnants removed, have attracted interest as scaffold material alternatives to simpler approaches where the scaffold is composed of a single material (Hoshiba et al. "Decellularized matrices for tissue engineering". Expert Opinion on Biological Therapy. 2010; 10:1717-28). Tissue decellularization results in a scaffold of extracellular matrix ideally suited for regenerating injured or diseased tissue since it retains the high resolution architecture and biological cues necessary for recapitulation of function. Decellularization may be done, for example, by using detergents, hydrogen peroxide, sodium hydroxide and enzymes, RNase and DNase. Particles can be manufactured by methods such as but not limited to colloid formation by hydrophilic/hydrophobic interactions, two phase emulsions and in oil interfaces. Fibers can be manufactured by methods such as but not limited to electrospinning, fiber extrusion and fiber pulling. Particles and fibers of any kind may be minced by any suitable method, exemplary and non-limiting methods including homogenizing, cryomilling, dry milling, cutting, chopping, crushing and slicing. These additive tissue pieces, particles and fibers may be further modified with functional groups binding to carrier polymer or combination of these materials or treated to expose reactive groups for crosslinking. Furthermore growth factors, antioxidants and drug molecules may be loaded in or on the added polymers, tissue pieces, particles and fibers.

Cells

The use of the term "cells" in this description encompasses not only individual cells, particularly mammalian cells, more particularly human cells, most particularly autologous human cells, but also encompasses agglomerations of the described cells which form spheroids, pellets, and microtissues, which are well known to and commonly used by the art. The cells for use in the method are advantageously cells of a similar type as those present on the cartilage tissue. Typical non-limiting examples of suitable cell types include primary autologous chondrocytes, primary allogenic chondrocytes, chondroprogenitor cells, chondroblasts, mesenchymal stem cells, induced pluripotent stem cells and adipose-derived stem cells, neural crest derived stem cells.

Printing Mix Material

The term "printing mix" in the context of the present specification refers to an extruded mass comprising the key constituent components:
  Particles made of natural (optionally: dried) tissue or fibre, or made of biocompatible, optionally bioresorbable, polymer, or both polymer and natural tissue/fibre,
  An aqueous solution of a gelling polysaccharide, particularly gellan gum or a derivative thereof, and
  Mammalian cells.

The composition of the printing mix material may be varied across a wide range, depending on the nature of the materials and the end-use. The polymers are typically present in a weight proportion of from 0.5-20%. When minced tissue, particles or fibers are present, they are typically present at a weight proportion of from 10-40% of dry polymers or equally 1-20% in total weight. When cells are present, they are typically used at concentrations of $3\times10^6$ cells/ml-$50\times10^6$ cells/ml.

In addition to the major components hereinabove described, the crosslinkable material may include other materials, present to confer particular properties on the material. One particular example is elastin, which is abundant in auricular and nasal ECM to provide the elasticity of the tissue and other examples include growth factors, cytokines, drugs, biologics, siRNA, DNA, antioxidants such as polyphenols into the polymeric solutions, which could augment regeneration of the tissues. Added growth factors could be bound to sulfated polymers or unmodified polymer for enhanced delivery and effectivity in the proximity of the cells residing in the printing mix.

The printing mix material in its ready-to-use form is a readily thermally gelled state that can easily be applied to take desired shape in the manufacturing process. Powders of the molecules and lyophilized minced tissue, particles and fibers can be stored and sterilized separately. All the components can be combined before packaging or rehydrated just prior to use thus preserving the growth factors and proteins for long periods of time.

Shape

Patient specific tissue grafts are tailored for each patient or certain model catalogs can be created for situations where patient imaging is not desired or not possible. The three-dimensional model obtained from external ear and nose scans can be modified to contain internal support structures, gradient of polymers for versatile mechanical properties and porosity for enhanced cell survival in large constructs. Furthermore region could be tuned in terms of stiffness, growth factor cocktail and concentration, for example, to induce regional variations in cell proliferation. For example the periphery of the cartilage graft could be more porous or softer allowing more nutrient flow into the deep structure. Also the regional specificity and tissue types are found in these constructs, for example, in the lobe of the ear fat is the main tissue and is responsible for the mechanical properties. The regional properties and specified structures can be easily built in a layer-by-layer manner. In such a layered approach, the crosslinking mechanism would take place not only within individual layers, but also between adjacent layers, thus forming a completely integrated continuous structure. This can be achieved by initiating crosslinking in the periphery of the construct in contact with support structure containing the reactive molecule reservoir.

Support

Support structure can be co-deposited with the printing mix material to support overhanging structures, to initiate crosslinking or to prevent drying of the material during deposition. Support material can contain crosslinking factors including but not limited to mono-, di-, trivalent cations, enzymes and radical initiators. Additionally, physical and physical-chemical methods may be employed by support material interactions to modify the pH and molecule concentration. After the construct manufacturing the support structure can be eluted. Elution can be due to but not limited to temperature change, pH change or degrading molecules.

The result is a cartilage repair that is quick, effective and long-lasting. The longevity is an important factor in the graft to preserve the mechanical properties until sufficient ECM production of the cells has been achieved to produce a native cartilage-like structure.

Typical examples of the use to which the method of this disclosure may be put include:
  Reconstruction of craniofacial defects;
  Filling and reconstruction partial tissue loss and integrating them with native tissue;

Reconstruction of trachea (windpipe), meniscus or costal cartilage with patient specific grafts;
Filling of osteochondral defects The method of the invention is characterized by the following advantages:
Possibility to produce patient specific tissue grafts for craniofacial and orthopaedic applications such as but not limiting to: ear, nose, articular cartilage.
Possibility to tune the bending properties to match the scaffold with physiological parameters and specific regions of the native tissue.
Possibility to include functional load bearing regions of more compact polymers and reinforced structures to tune the mechanical properties of the graft.
Provides better patient satisfaction and decreased pain levels due to elimination of the need for cartilage harvest.
Utilizes autologous, allogenic or xenogenic native tissue which already contains the complex array of tissue-specific extracellular matrix components in physiologically accurate proportions. These particles are mainly responsible of the proliferation cues stimulating the chondrocytes.
Tissue fragments from any possible ECM particles can be incorporated into hydrogel blend for additive manufacturing purposes to produce any desired geometry without compromising its biochemical composition thus rising prospects for organ bioprinting.
Possibility to incorporate therapeutic factors within the scaffold including, but not limited to: pharmaceutical compounds, growth factors, peptides, proteins, carbohydrates, and gene therapy vectors. Additionally, homing molecules can be included that would induce host cell migration into the scaffold.
Possibility to achieve zonal organization of tissue architecture by layering various tissues/compositions using additive manufacturing techniques.

EXAMPLES

Example 1a: Bioprinting of Patient Specified Tissue Wafts

Figure 1A:
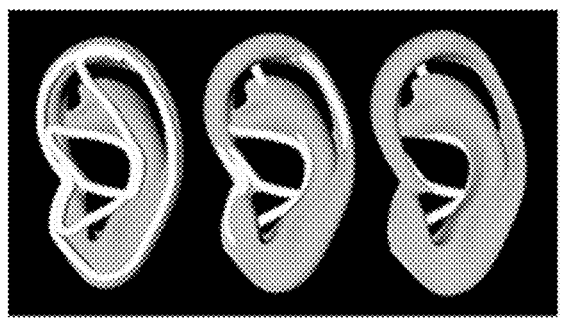
FIG. 1A is the three dimensional model created based on patient CT models and after internal support structure was added for better load bearing to the graft.
Figure 1B:
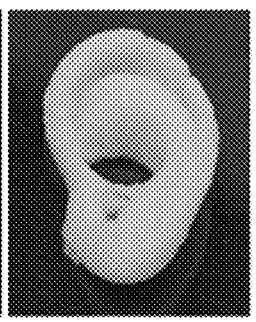
FIG. 1B is a photograph of an intact tissue engineered ear construct.
Figure 1C:
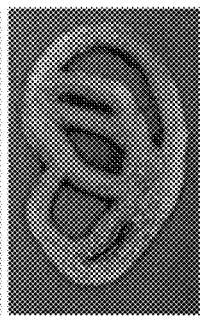
FIG. 1C is a photograph of internal support that could stabilize the ear structure for more natural like bending properties. Both images B and C were fabricated utilizing three-dimensional bioprinting and are composed of minced cartilage particles, gellan gum, and alginate.
Figure 2:
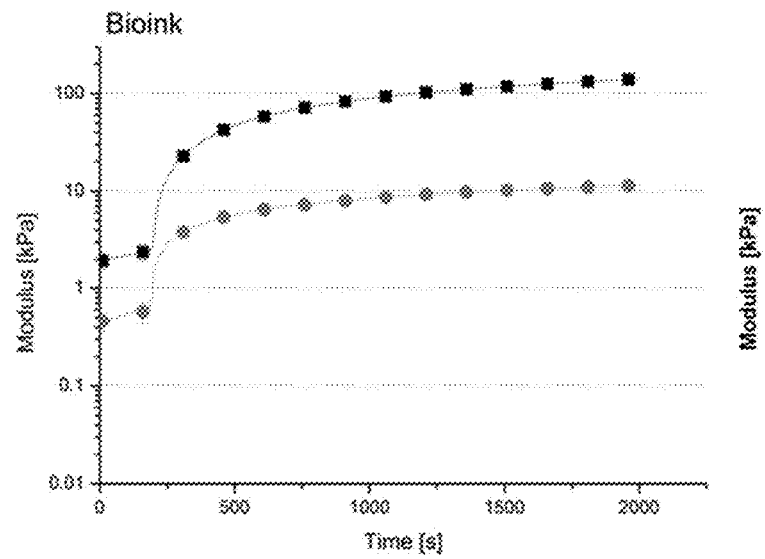
FIG. 2 shows graphs illustrating the rheological crosslinking kinetics and the final stiffness of the bioink with two compositions (Bioink, top panel; Bioink+HA, bottom panel).
Figure 2:
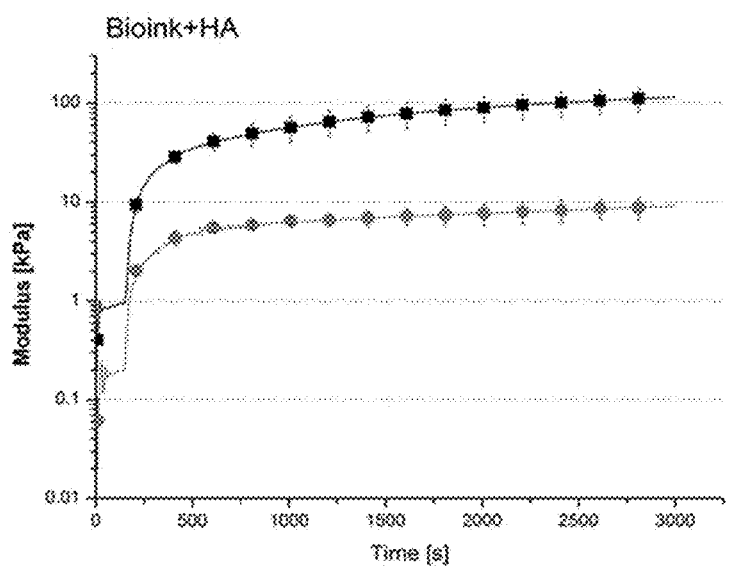

Clinical computed tomography imaging was performed and the resulting computational three-dimensional object (FIG. 1) was obtained. The patient specific external ear model was then mirrored for the contralateral side and a new 3D model was generated. Together with the new model the external support structure model was generated to support the ear structure especially in the overhanging regions during the printing. Support structure was designed to be in contact with the ink in the strategically important places to initiate the crosslinking and to support the overhanging features (FIG. 5). The co-extrusion of the support material was shown to preserve horizontal bioink lines without sagging and the printed shape accurately after elution of the support. Furthermore the internal support structure of more dense polymers was prepared to allow better force distribution in internal structure (FIG. 2, 3). All models were converted into machine code in STL-converter (RegenHU) and transferred into the bioprinter (BioFactory, RegenHU) for the printing process.

Using the same technique the inventors have demonstrated the printing of several cartilaginous structures including meniscus, intervertebral discs and nose. Two-component intervertebral disc grafts could be printed with two bioink compositions mimicking the nucleus pulposus and the annulus fibrosus.

Example 1b: Production of Cartilage Particles for Three-Dimensional Printing Purposes Cartilage was harvested from the fresh bovine articular or auricular cartilage by removing thin layers of cartilage into a petri dish containing PBS and penicillin-streptomycin 1%. The harvested cartilage was transferred into cryomill (Retsch) and milled for three cycles in 30 Hz intensity. Milled cartilage was collected and lyophilized to obtain dry powder that could be sieved into the desired particle size range. These particles can be further loaded with growth factors or other molecules to enhance the proliferation and other cell responses. After loading the particles were lyophilyzed and cryopreserved to maximize the biomolecule availability for prolonged shelf life.

Example 1c: Printing Mix Material Preparation and the Printings Process

Printing mix material ("Bio-Ink") was produced by combining gellan gum in 3.5% concentration with the alginate 3%. Gellan gum was dialyzed against ultrapure water to minimize the cation residues in the material. Dialysis was performed over three days in 70-80° C. ultrapure water changing the water one to two times a day. Gellan was further lyophilized to obtain a dry powder. Purified gellan gum was dissolved into glucose containing deionized water making it more cell compatible and alginate solution was added to obtain final concentration of polymers. The polymer blend was mixed with ECM particles and $6 \times 10^6$ cells/ml to obtain the final printing mix material. This printing mix material stimulated the cell proliferation significantly compared to positive control (FIG. 4). Cartilage extracellular matrix production was evaluated with histology and immunostaining after 8 weeks in culture for Bioink alone and Bioink+ECM with and without growth factor TGF-β3. The Bioink+ECM without growth factors stimulated cell proliferation above Bioink alone which was clearly visible in H&E staining. The Bioink+Cartilage particles showed a slight increase in Alcian blue staining and a slight collagen II staining was observed suggesting the need for additional growth factor stimulation. Cells were often seen proliferating around the particles without growth factor whereas the Bioink+Cartilage particles with TGF-β3 had no site-specific proliferation which suggests that the particles are a source of mitogenic growth factors. After 8 weeks, the gross appearance of the scaffolds suggested that the growth factor stimulation had a clear effect on cartilage matrix production as seen in the size and opaque appearance of TGF-β3 supplemented samples. Both supplemented bioink compositions showed a significant increase in cartilage ECM components and had areas which began to resemble the cell density and GAG content of native cartilage. Furthermore, collagen II deposition was strong throughout the graft in the growth factor supplemented conditions while only pericellular staining was seen in the samples cultured without TGF-β3. Collagen type I and alizarin red staining were performed to determine the fibrocartilage production and calcification. Collagen I was found in Bioink+Cartilage particles and in both TGF-β3 supplemented conditions suggesting some fibrocartilage production, perhaps due to the passaging of the cells. In all the conditions calcification was absent suggesting the cartilage phenotype of the chondrocytes was stable.

The printing mix material was printed onto a substrate and the support polymer Pluronic F127 was co-extruded to fill subsequent layer. Pluronic contained 20 mM of $SrCl_2$ to initiate the bioink crosslinking upon contact with the ink. Cations diffused into the printing mix material due to osmotic balance and electrostatic forces which initiated the crosslinking. Structures were generated with 410 μm needles and 800 mm/minute feedrate. Pressure applied to extrusion syringe varied between 1.2-1.4 bar. After layer-by-layer deposition of the material into desired form, the sacrificial support Pluronic was eluted in a 20 mM $SrCl_2$ bath for few minutes before the construct was transferred to 37° C. cell culture medium. FIG. 1 illustrates the ear cartilage internal support structure and FIG. 6 shows the nose grafts generated by this technique. FIG. 2 illustrates the initial storage modulus being 100 kPa after crosslinking which is comparable to high stiffness hydrogels.

Example 2: Bioink Composition Optimized for its Mechanical Properties and Growth Factor Retention Bioink preparation: Gellan was added to D-glucose (300 mM) containing ultra-pure water at 90° C. to achieve a 3.5% solution, of which 85% was low-acyl gellan gum and 25% was high-acyl gellan gum. Alginate was added to the mixture to achieve 2.5% solution. The boiling flask was kept at 90° C. with agitation until the solution was homogeneous, typically for one hour. The homogeneous solution was cooled down to 30° C. prior the cell mixing. Briefly, the bovine chondrocytes ($4 \times 10^6$ cells/a) were mixed in the DMEM solution and added to the bioink in culture medium in 1:10 volume ratio to pre-crosslink the bioink. Mixing was performed until the solution reached room temperature and the printing syringes were loaded.

Gellan gum high acyl (GG-HA) and low acyl (GG-LA) compositions (FIG. 8) contribute to the stiffness and the elasticity of the final bioink. By varying the ratio between the acylation forms the materials can crosslink tighter yielding stiffer matrix whereas by disrupting the tight packing of the polymer chains in crosslinking more elastic matrix can be produced. These parameters were optimal for craniofacial applications in 85% GG-LA, 25% GG-HA composition which provides tunable crosslinking properties up to 230 kPa ultimate stress and an average strain of 68% at failure (FIG. 3). To further optimize the growth factor retention in the bioink a concentration of 2% of sulfated gellan gum (GG-3%) (FIG. 8) was added to the bioink. This composition was superior in retaining the loaded growth factors, in this case TGF-β3 and FGF-2, in the bioink compared to the non-sulfated bioink.

Example 3: Optional Printing Material and Crosslinking Process with Support Material Base polymer gellan 3% with additive hyaluronan conjugated with tyramine 3% were mixed together to generate enzymatically crosslinkable hydrogel in the presence of horseradisch peroxidase (HRP) and hydrogen peroxide. Materials were dissolved into deionized water in presence of monosaccharide glucose in physiologic osmolarity, specifically 300 mM. Hydroxyapatite particles in concentration of 4% (w/v) were added to the polymer mixture. This bio-ink composition was further bioprinted in the presence of HRP and hydrogen peroxide when HRP was mixed either to the bio-ink in 1 unit/ml concentration or to the pluronic F127 30% mixture together with the hydrogen peroxide in 0.0012% concentration. Layer-by-layer constructed scaffold crosslinked immediately upon contact with the support structure. The support structure was eluted in the cold medium to decrease the negative effects of hydrogen peroxide in the presence of the cells. The structure was washed several times after to minimize the amount of hydrogen peroxide residues.

Example 4: Fiber Reinforced Materials for Bioprinting

Gellan 3% was dissolved in deionized water and 10% (w/v) polymethyl metacrylate (PMMA) fibers were added as chopped eletrospun fibers into the gellan solution. Fibers were imaged with scanning electron microscopy to determine the fiber diameter to be approximately 2 micron. The fiber reinforced gellan was imaged before the shear (FIG. 7 left) and after two different shear orientation for 2 minutes (FIG. 7 middle and right). Fiber orientation was greatly increased in uniaxially shear already after 2 minutes. Furthermore, the uniaxial but not unidirectional shear oriented the fiber shorter than 50 microns to shear direction, thus allowing us to form heterogeneous load bearing structures in the matrix. However, fibers longer than 50 microns were not able to keep the orientation in shear when direction of shear was altered. During the extrusion printing the shear pattern is uniaxial and unidirectional in the nozzle, thus orientating the fibers to flow direction. Upon fast cessation of flow we can keep the fiber orientation uniaxial which will affect the load bearing capability of the structures. These structures are nature inspired and for example collagen II fibers in articular cartilage are changing the orientation in different cartilage layers.

Example 4a Bioink Crosslinking

An exemplary bioink is a blend of gellan and alginate mixed with human micronized Cartilage particles or HA particles (≤40 μm size). Upon addition of mono-, di- or trivalent cations, gelation (sol-gel transition) occurs as the helices aggregate into junction zones which are linked into a three dimensional network via the coiled part of the molecule. The printing process is divided into three stages namely bioink pre-printing, printing process and post-printing crosslinking. Initially the bioink was loaded into a syringe and the support polymer into a second syringe. At this stage, a small amount of cations were present in the bioink to increase viscosity and enhance printing properties. During the printing process the co-extruded of the support, cations diffused to the periphery of the printed structures to initiate the crosslinking. After the final structure is completed, the support can be eluted in 4° C. cation-supplemented medium.

Example 4b: Rheological Analysis

The cation related viscosity enhancement and crosslinking properties can be investigated with rheology and mechanical testing. Rheological properties of the Bioink, Bioink+HA, and Bioink+Cartilage Particles were measured with an Anton Paar MCR 301 (Anton Paar, Zofingen, Switzerland) rheometer to determine the shear behavior and shear recovery. All of the bioink compositions showed shear thinning behavior which is critical for extrusion (FIG. 11*a*). Furthermore, all the compositions had a yield point (weak gel formation) prior to extrusion which is important in preventing particle and cell sedimentation in the syringe (Table 1).

TABLE 1

Summary of the rheological measurements. The yield points were calculated using the Herschel/Bulkley equation.

|  | Bioink | Bioink + HA | Bioink + Cartilage Particles |
|---|---|---|---|
| Yield point | 15.6 Pa ± 0.7 Pa | 17.7 Pa ± 6.5 Pa | 122 Pa ± 22 Pa |
| Cessation in 10 s* | 21% | 90% | 98% |
| Maximum G' | 152 kPa ± 3.0 kPa | 110 kPa ± 2.0 kPa | 96 kPa ± 1.0 kPa |

*Shear recovery at 10 s after the 2nd shear sequence.

The shear recovery curves (FIG. 11b) illustrate the recovery of the bioink structure after the printing process. Shear recovery after the second shear sequence was 98% in Bioink+Cartilage Particles and 90% in Bioink+HA after ten seconds. At the same time the Bioink alone recovered to only 21% of the original modulus. FIG. 11c illustrates the storage modulus G' after cation-induced crosslinking of Bioink alone where the cation concentration and source had a clear influence. FIG. 11d illustrates the final storage modulus for the three bioink compositions. The Bioink alone had the highest final storage modulus (152 kPa±3 kPa) compared to Bioink+Cartilage Particles (96 kPa±1 kPa) and Bioink+HA (110 kPa±2 kPa), suggesting that crosslinking is somewhat hindered by the particles irrespective of their source.

Example 4c: Mechanical Properties and Swelling Behavior

Mechanical properties of the bioprinted cartilaginous structures were assessed in tension. Tensile dumbbell specimens were printed using Bioink+HA particles with or without cells. The nozzle path (printing direction) in the gage section of the specimen was chosen to be parallel to the direction of tension (FIG. 12a). Young's modulus was significantly higher in acellular constructs (E=230 kPa±7.0 kPa) compared to cellular ones (E=116 kPa±6.8 kPa) (p<0.001), suggesting that the cells increase the compliance of the construct and/or inhibit the crosslinking. There was no difference in failure strain between the acellular (37%±6.4%) and cellular (34%±2.1%) (p=0.54) constructs.

Figure 12C:
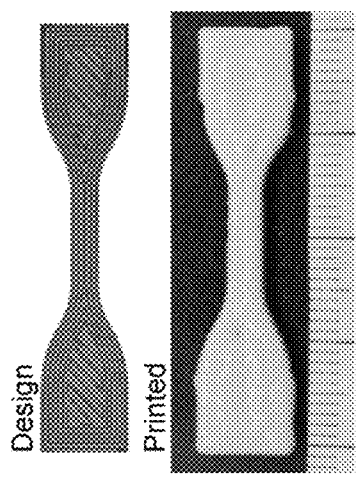
Figure 12D:
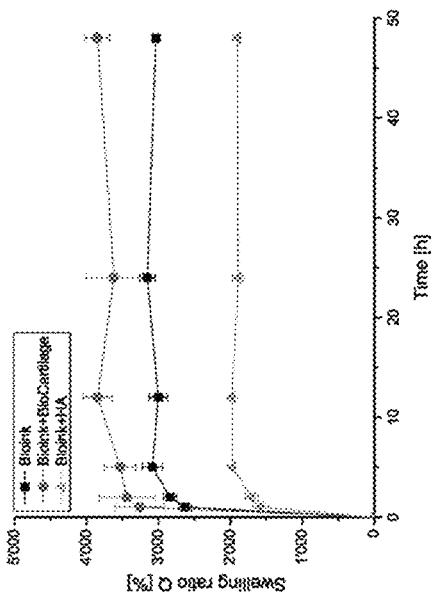

Swelling of the bioink with and without particles was quantified to assess the total water retention and the water retention after gel crosslinking (FIG. 12c-d). Swelling at 37° C. up to 48 hours increased the hydrogel weight between 2000-3800% of the dry weight of the sample which is typical of hydrogels and between 26% and 54% of the crosslinking weight of the hydrogels. Fully hydrated state was achieved after 24 hours and in more specific the Bioink and Bioink+Cartilage particles were fully hydrated after 5 hours suggesting faster swelling kinetics. Comparison between swelling ratios of the Bioink alone and the particle containing compositions after 48 hours suggested dependency on the particle type.

Example 4d: Bioink Compatibility

Cellular bioprinting process was investigated with Bioink+HA to exclude all the interactions and proliferation cues between particles and cells. One layer thick discs were printed to assess the cell viability after printing (FIG. 13a) which was compared to the initial viability of the cells prior to mixing. To investigate cell viability in large structures, a young adult sized nose (3.1 cm, 2.6 cm and 1.5 cm) was printed and kept in static culture until the cell viability in the middle of the construct was evaluated from a central slice (minimum diffusion distance of 5 mm). Bioprinting with the particles showed an 80% viability three hours after printing, however, after four days the cell viability recovered to 97% where it remained until the end of the experiment. The young adult sized nose graft had decreased viability in the center of the scaffold (60% viable cells at day 7) compared to 96% viability in the periphery (FIG. 13b). This suggests the need for incorporating internal porosity or channels to enhance nutrition transport. By introducing interconnected porosity into 1.5 cm high cubes the viability in the center of the structure was as high as in the periphery. Such nutrition channels for engineered porosity can be incorporated into the bioprinted structures by extruding the support polymer within the grafts, which could later be cleared in subsequent washing/crosslinking steps. With this technique a complex 3D interconnected porous network can be created that is used to perfuse the grafts with nutrient-rich medium. To further enhance mass transport of nutrients, grafts can also be pre-conditioned in dynamic bioreactors.

The effect of cartilage particles and growth factor, in this case TGF-β3, supplementation on cell proliferation was evaluated in casted gels cultured for 21 days. The Bioink alone did not stimulate cell proliferation; in fact there was a loss in DNA at day 7 which slowly recovered. Bioink+Cartilage particles, on the other hand, stimulated proliferation and caused a statistically significant increase (p<0.001) in DNA over 21 days. With TGF-β3 supplementation, there was a statistically significant increase in DNA in the Cartilage particles containing samples at day 7 (p<0.001). By day 21, both bioinks showed increases in DNA, which were not statistically significantly from each other.

Example 4e: Extracellular Matrix Production and Cartilage Formation

Cartilage extracellular matrix production was evaluated in bioink alone and bioink+Cartilage particles with histology and immunostaining after 3 and 8 weeks in culture. Histological evaluation after 3 weeks revealed a clear increase in cell number, GAG synthesis and collagen II production in both bioink compositions supplemented with TGF-β3 (10 ng/ml). Furthermore, Bioink+Cartilage particles without growth factors stimulated cell proliferation above Bioink alone which was clearly visible with 3 and 8 week H&E staining. At both time points the Bioink+Cartilage particles showed a slight increase in Alcian blue staining and at the 8 week time point a slight collagen II staining was observed suggesting the need for additional growth factor stimulation. Cells were often seen proliferating around the particles without the growth factor supplementation which suggests that cell-particle adhesion and/or growth factors in the particles are important. However, because in the Bioink+Cartilage particles with TGF-β3 samples, no site-specific proliferation was observed, the results suggest rather the particles are a source of mitogenic growth factors and not specific cell-matrix adhesive cues. After 8 weeks, the gross appearance of the scaffolds suggested growth factor stimulation had a clear effect on cartilage matrix production as opaque appearance and increase in size was observed. At 8 weeks, both supplemented bioink compositions showed a significant increase in cartilage ECM components and had areas which began to resemble the cell density and GAG content of native cartilage. Furthermore, collagen II deposition was strong throughout the graft in the growth factor supplemented conditions while only pericellular staining was seen in the samples cultured without TGF-β3. Collagen I was found in Bioink+Cartilage particles and in both TGF-β3 supplemented conditions suggesting some fibrocartilage production, perhaps due to the passaging of the cells. In all the conditions calcification was absent suggesting the cartilage phenotype of the chondrocytes was stable.

Example 4f: Magnetic Resonance Imaging

To assess the shape retention of the printed structures several MRI techniques were evaluated. The printed nose was kept in PBS for 2 weeks to assure complete swelling prior T2-weighted MR imaging. These images were thresholded and converted into a .STL file and compared to the original model used for printing and to the cartilaginous graft immediately after printing. Comparison of the original model and the printed graft illustrates precise material extrusion and detailed structures. However, slightly thicker nostril walls were observed in comparison to the original model. Furthermore, when comparing the printed structure to the MRI model after 2 weeks swelling, a slight thickening of the nostril walls were observed, however, no sign of degradation or deterioration of the shape was detected.

Example 5: Bioprinting Process Parameters

One important factor of the reproducible printing process is the connectivity of the consecutive lines. In order to assess the effect of line spacing an optimization of line thickness must be conducted. Printing parameters such as pressure, feed rate and needle diameter were tested to standardize the line thickness to 900 μm±53 μm. After the determination of the average line thickness the effective line-line adhesion was investigated by printing a series of tensile testing dumbbells having different line spacing. The dumbbells were tensile tested until failure and the data illustrates that by increasing the line spacing the possibility of defects in the structure increased suggesting that in order to provide reproducible mechanical properties for printed structures the lines should overlap approximately 40-50%. The data suggested that the variance of the ultimate stress at failure did not differ in the tested samples with amount of overlapping lines down to 20% whereas the number of samples that were not stabile enough for testing increased with increasing line spacing. According to the data the optimal line spacing is affected by the bioink in question however by increasing the overlapping the probability of internal printing process related defects decreases. Furthermore the line thickness can be freely chosen by changing the process parameters such as pressure, printing speed and needle diameter.

Several mechanical testing measurements were performed for the newly designed bioink to investigate the parameters affecting the reproducibility of the structural and mechanical properties. The tensile evaluation of specimens printed with varying printing directions and with cell laden bioink revealed that the youngs modulus, ultimate stress and the failure strain are not altered by adding of the cells in the seeding density of $4 \times 10^6$ illustrating that the volume fraction of cells (~1% approx.) is compensated by the strong surrounding matrix. Furthermore, dumbbell specimens were printed in varying printing directions with respect to the tension, namely parallel to tension (0°), perpendicular to tension(90°) and in 45° angle to the tension (45°). The printing direction did not show any statistically significant differences between the groups suggesting that the bio-printed structures can be designed based on the printing and process related parameters rather than based on the estimated mechanical loading of the final structures.

We claim:

1. A graft scaffold comprising:
   3% to 3.5% (w/v) of a gelling polysaccharide selected from the group consisting of gellan gum, acylated and sulfated gellan gum;
   mammalian cells; and
   alginate,
   wherein the graft scaffold is obtainable by a method comprising:
   providing an aqueous solution of the gelling polysaccharide and alginate;
   providing mammalian cells;
   mixing said aqueous solution of a gelling polysaccharide and alginate, and said mammalian cells to obtain a printing mix; and
   depositing said printing mix in a three-dimensional form, thereby obtaining the graft scaffold.

2. The graft scaffold of claim 1, wherein the alginate concentration is 2.5% or 3% (w/v).

3. The graft scaffold of claim 1, wherein said gelling polysaccharide is acylated gellan gum.

4. The graft scaffold of claim 1, wherein said aqueous solution of a gelling polysaccharide and alginate further comprises between 10 and 150 mmol/l of divalent ions.

5. The graft scaffold of claim 1, wherein the graft scaffold further comprises
   particles selected from the group consisting of ECM, cartilage, hydroxyapatite (HA), polymer, biocompatible conductive material, and calcium phosphate; and/or
   fibres selected from the consisting of silk, elastin, and resilin.

6. The graft scaffold of claim 1, wherein the graft scaffold does not comprise particles selected from the group consisting of ECM, cartilage, hydroxyapatite (HA), polymer, biocompatible conductive material, and calcium phosphate or fibres selected from the consisting of silk, elastin, and resilin.

7. The graft scaffold of claim 1, wherein said aqueous solution of a gelling polysaccharide and alginate further comprises a monosaccharide sugar or disaccharide sugar at physiologic osmolarity.

8. The graft scaffold of claim 1, wherein the graft scaffold further comprises a growth factor and/or a mitogenic factor.

9. The graft scaffold of claim 8, wherein the growth factor or mitogenic factor is selected from the group consisting of BMP-2, BMP-7, TGF-β1, TGF-β2, TGF-β3, FGF-2, and IGF-1.

10. The graft scaffold of claim 8, wherein the concentration of growth factor and/or mitogenic factor is 0.1-5 ng/ml, 5-50 ng/ml or 50-500 ng/ml.

11. The graft scaffold of claim 1, wherein said mammalian cells are cartilage cells, cartilage stem cells, or cartilage precursor cells.

12. The graft scaffold of claim 1, wherein said mammalian cells are present at concentrations of $3 \times 10^6$ cells/ml — $50 \times 10^6$ cells/ml.

13. The graft scaffold of claim 1, wherein the graft scaffold comprises 10 ng/ml TGF beta 3.

14. The graft scaffold of claim 1, wherein depositing said printing mix in a three-dimensional form is performed by deposition of lines of said printing mix, wherein each line has a width of 700 to 1100 μm and said lines overlap by 20% to 60%.

15. The graft scaffold of claim 1, wherein said depositing is performed by 3-D-printing methods.

16. The graft scaffold of claim 1, wherein said depositing is performed by additive manufacturing methods.

17. The graft scaffold of claim 16, wherein the additive manufacturing method is ink jet printing, bioprinting, extrusion printing or layer-by-layer method.

18. The graft scaffold of claim 1, wherein the 3-Dimensional form is generated based on a computer model of a contralateral organ.

\* \* \* \* \*